US00PP26982P3

(12) United States Plant Patent
Smith et al.

(10) Patent No.: US PP26,982 P3
(45) Date of Patent: Jul. 26, 2016

(54) ***ASCLEPIAS* PLANT NAMED 'CHARLOTTE'S BLUSH'**

(50) Latin Name: *Asclepias curassavica*
Varietal Denomination: Charlotte's Blush

(71) Applicants: Edith Smith, Brooker, FL (US); Charlotte MacCallum, Brooker, FL (US)

(72) Inventors: Edith Smith, Brooker, FL (US); Charlotte MacCallum, Brooker, FL (US)

( * ) Notice: Subject to any disclaimer, the term of this patent is extended or adjusted under 35 U.S.C. 154(b) by 198 days.

(21) Appl. No.: 13/998,682

(22) Filed: Nov. 22, 2013

(65) Prior Publication Data

US 2015/0150170 P1 May 28, 2015

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

(56) References Cited

PUBLICATIONS

Drotleff Hort Couture Boosts Butterflies with 'Monarch's Promise' and Gediflora Provides Mum Production Secrets. Greenhouse Grower 2015, retrieved from the Internet at <http://www.greenhousegrower.com/varieties/hort-couture-boosts-butterflies-with-monarchs-promise-and-gediflora-provides-mum-production-secrets/#/BlackoutGallery/69137/4/> 8 pp.*

* cited by examiner

*Primary Examiner* — June Hwu
(74) *Attorney, Agent, or Firm* — Thomas | Horstemeyer, LLP

(57) ABSTRACT

A distinct cultivar of *Asclepias* plant named 'Charlotte's Blush', characterized by its white, cream, pink, and green variegated leaves and seed pods; blooms are brightly colored; it grows well in full sun to light shade.

4 Drawing Sheets

BACKGROUND OF THE INVENTION

Figure 1:
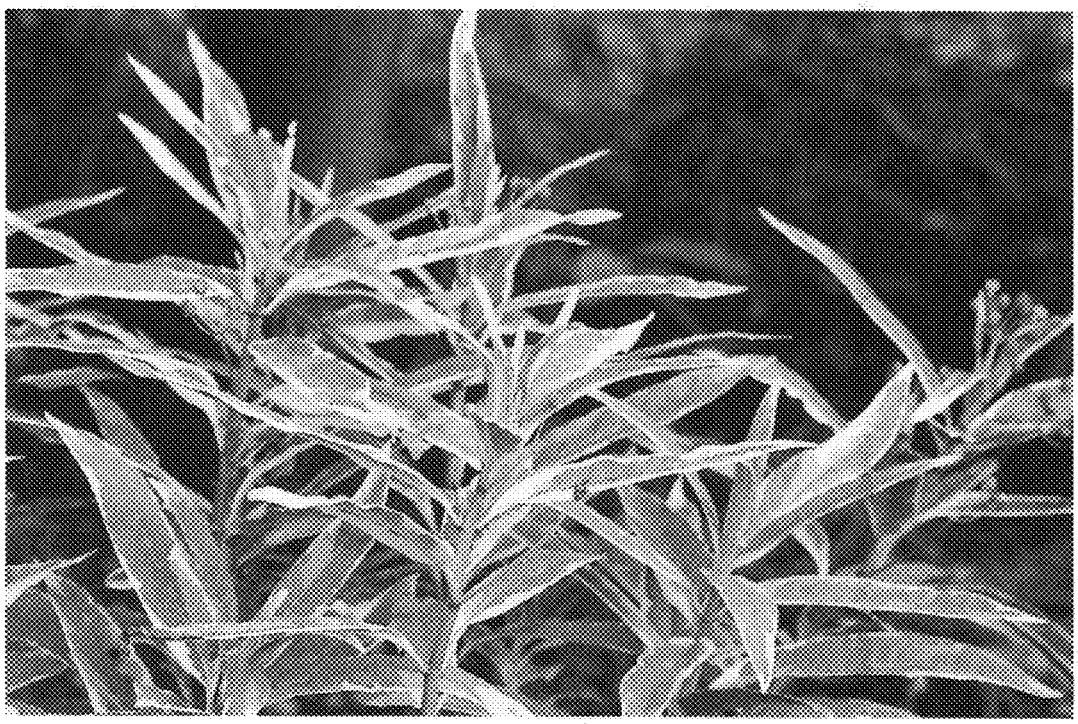

The present invention relates to a new and distinct cultivar of *Asclepias* plant, botanically known as *Asclepias curassavica*, and hereinafter referred to by the cultivar name 'Charlotte's Blush'.

The new *Asclepias* was discovered as a sport of an *Asclepias curassavica* in the Inventor's butterfly farm garden in Brooker, Fla. in the spring of 2012, and differs from the parent *Asclepias curassavica* in the presence of variegated leaves and seed pods in shades of green, cream, beige, and yellow that also exhibit tinges of pink coloration.

Asexual reproduction of the new cultivar was first accomplished by stem cuttings taken at the butterfly farm garden in Brooker, Fla. in the spring of 2012. Several hundred plants of the new cultivar were grown from stem cuttings for over a year and several generations. This continued propagation has shown that the unique characteristics of this cultivar are stable and reproduced true to type via cuttings in successive generations.

SUMMARY OF THE INVENTION

Plants of the cultivar 'Charlotte's Blush' have been grown under low light and high light conditions. The phenotype may vary somewhat with variations in environment such as light intensity and temperature. Under some light and temperatures, the intensity of the pink color will vary, such as being less intense when grown in low sunlight and more intense when grown in full sun. It has been grown in pots and in soil.

The following traits have been repeatedly observed and are determined to be the unique characteristics of 'Charlottes Blush'. These characteristics in combination distinguish 'Charlotte's Blush' as a new and distinct cultivar of *Asclepias*.

1. 'Charlotte's Blush' exhibits variegated leaves with centers in shades of green that may vary from light to dark and with creamy margins and central vein in shades of cream, beige, and/or yellow, with tinges of pink and/or fuchsia.
2. 'Charlotte's Blush' exhibits variegated seed pods that include two or more of the following colors: pink; green shades, light to dark; cream/beige, and yellow.

'Charlotte's Blush' was observed to be unique from the parent *Asclepias curassavica* plant from which it was derived, and from all other known *Asclepias curassavica* cultivars, in having distinct leaf variegation and seed pod variegation including, in addition to shades of green, shades of cream, beige and/or yellow and shades of pink and/or fuchsia. The pink coloration is more intense when grown in high light. All other known *A. curassavica* plants and even other species have solid green leaves. Like other *Asclepias curassavica*, 'Charlotte's Blush' also has orange blooms, as described in greater detail below.

In addition, 'Charlotte's Blush' grows well in full sun to light shade, blooms with bright orange and yellow flowers, and has uniform flowering within the florescence. Plants of the cultivar 'Charlotte's Blush' also grow well in pots as well as in the ground and exhibit good post-production longevity.

BRIEF DESCRIPTION OF THE PHOTOGRAPHS

The accompanying colored photographs illustrate the overall appearance and distinct characteristics of the new cultivar showing the colors as true as possible. Colors in the photographs may differ slightly from the color values cited in the detailed botanical description which accurately describes the colors of the new *Asclepias*. The photographs were taken of plants grown outdoors in Brooker, Fla.

The photograph in FIG. 1 is a side view of 'Charlotte's Blush' growing in the ground in full sun. The photograph shows the variegated leaves of 'Charlotte's Blush'.

Figure 2:
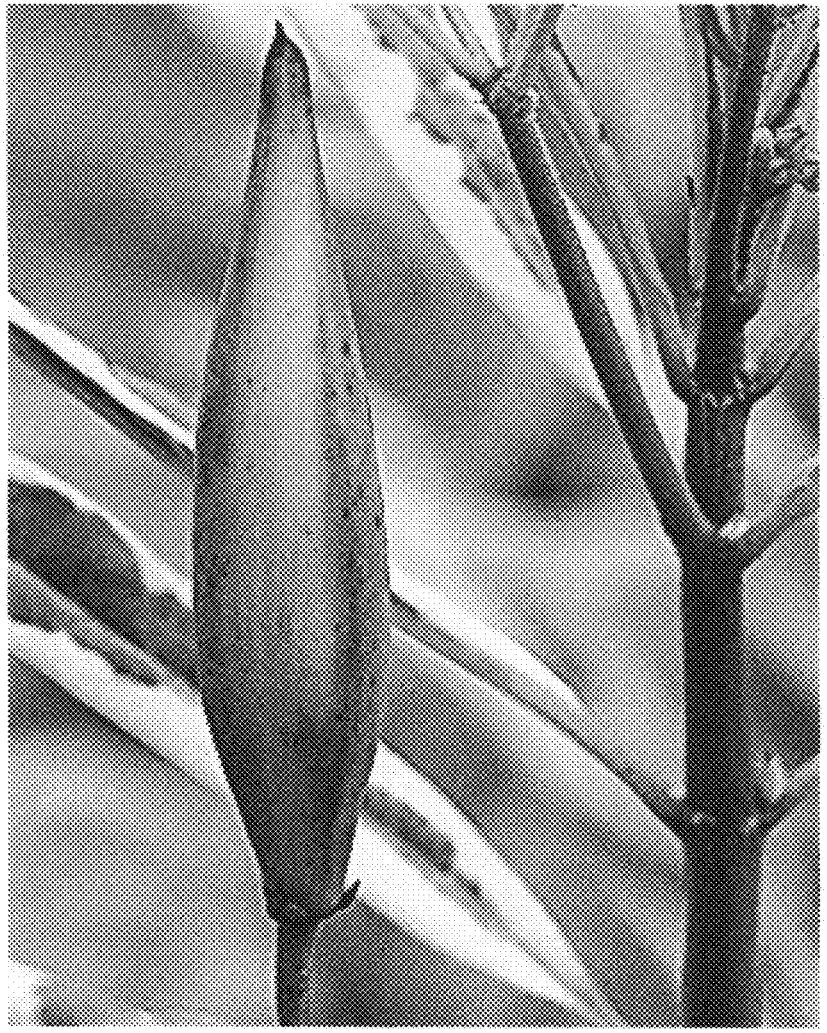

FIG. 2 is a photograph of a close-up view of a seed pod of 'Charlotte's Blush' growing in the ground in full sun. The cream and green variegation is visible in this photograph, as well as pink coloration on the tip of the seed pod.

Figure 3:
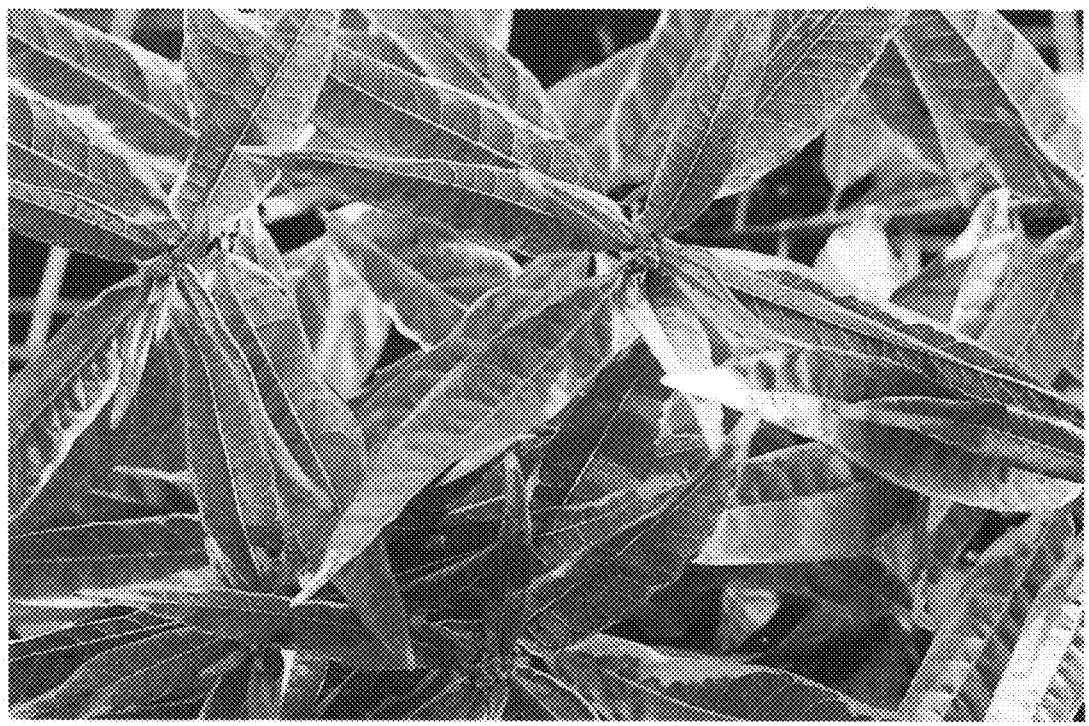

The photograph in FIG. 3 shows 'Charlotte's Blush' growing in a pot in partial shade. Pink and fuchsia are more visible among the white, cream, and green leaves in this photograph. Although the intensity of the pink coloration tend to be more intense in plants grown in full sun, the color shows better in photographs taken in lower light.

Figure 4:
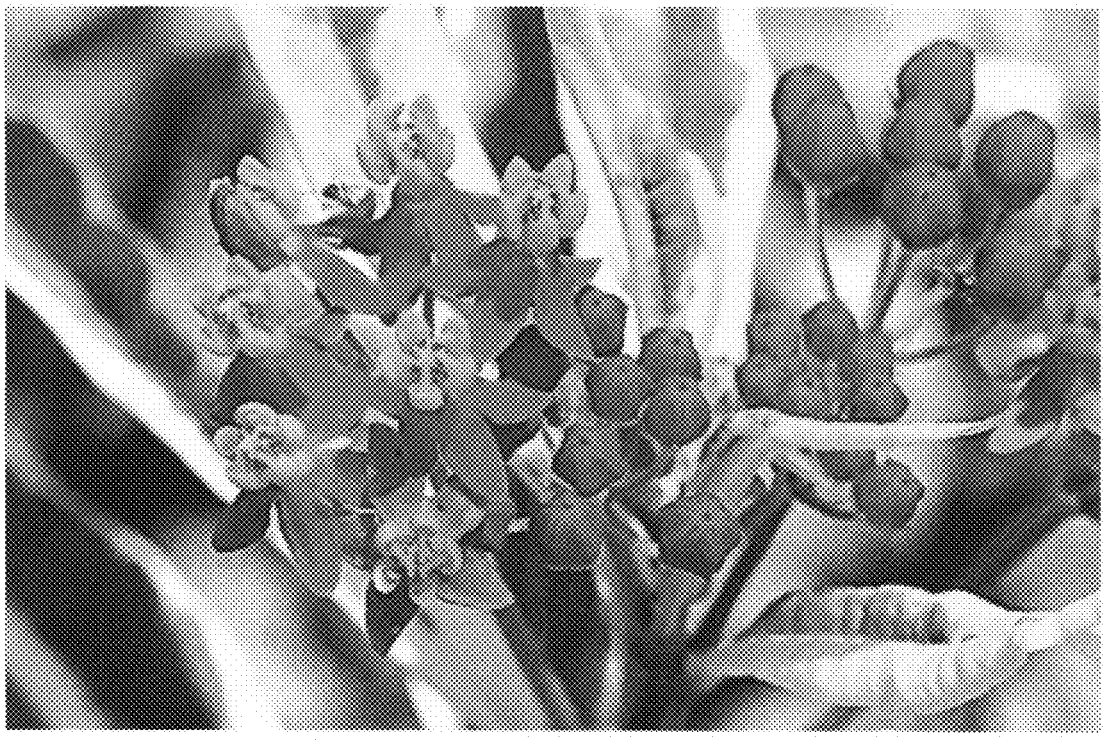

FIG. 4 is a close-up photograph of blooms of 'Charlotte's Blush' growing in the ground in full sun, with the variegated leaves visible in the background.

DETAILED BOTANICAL DESCRIPTION

The following observations, measurements, and values describe plants of the new cultivar grown as stem cuttings at the butterfly farm garden in Brooker, Fla. The plants were grown under average day temperatures of 15° to 48° C. and average night temperatures of 1.6° to 26° C. The phenotype of the new cultivar may vary with variations in environmental, climatic and cultural conditions.

Color references are made to The 2005 R.H.S. Mini Colour Chart (The Royal Horticultural Society, 80 Vincent Square, London SW1 P 2PE, United Kingdom), except where general terms of ordinary dictionary significance are used.

Botanical classification: *Asclepias curassavica* 'Charlotte's Blush'.

Parentage: Sport from *Asclepias curassavica.*

Growth and propagation:

- *Growth rate*.—Vigorous; roots well with or without rooting hormone.
- *Propagation type*.—Stem Cuttings.
- *Root description*.—Fibrous.

Plant description:

- *Form*.—Upright flowering perennial/annual.
- *Hardiness*.—Zone 8b and warmer as perennial; annual in cooler zones.
- *Usage*.—Garden, Monarch butterfly and Queen butterfly host plant, container gardens.
- *Vigor*.—Moderate.
- *Flowering period*.—Six weeks from liner to bloom; blooms till first frost.
- *Height and spread*.—Grows to 36" tall and 24" wide.
- *Stems size*.—Grows to ½ diameter and 24" long.
- *Stem shape*.—Round.
- *Stem color*.—Blend of 164C and 137C.
- *Stem surface*.—Smooth.
- *Stem strength*.—Strong.
- *Internode length*.—Depends upon light conditions, but average of 2 to 3".
- *Branching habit*.—Freely branched; additional branches readily grow, especially when pruned.
- *Petiole*.—Average length: 10 mm; general shape is split cylinder, with a smooth surface texture; color: 140D.

Foliage description:

- *Leaf shape*.—Linear.
- *Leaf division*.—Single.
- *Leaf base*.—Rounded.
- *Leaf venation*.—Parallel.
- *Leaf margins*.—Entire, slightly sinuate.
- *Leaf arrangement*.—Opposite.
- *Leaf color*.—Variegated with centers a random mixture of 137A and 194A, both upper and lower surfaces of the leaf; margins mixture of 8C and 15D with 160B, moving from one color to another randomly; young leaf color generally the same as older leaves; margins tinged with 70C, with possible tinges of 77B (depending upon temperature/light).
- *Leaf number*.—Average of 20 to 30 per lateral branch.
- *Leaf size*.—2" to 4" in length.
- *Leaf aspect*.—Angle about 25-35 degrees upward from stem.

Flower description:

- *Flower type and habit*.—Multiple florets on raceme.
- *Inflorescence type*.—10-20 florets on a raceme.
- *Inflorescence size*.—1-2 inches.
- *Inflorescence lastingness*.—About 14 days.
- *Flower shape and color*.—Red and dark pink red corollas (color 47A and 53C respectively) and yellow/orange corona lobes (color 23A).
- *Flower fragrance*.—None.
- *Flower arrangement/appearance*.—Cymes with 10-20 flowers each.
- *Bud*.—Color: 67A; the shape is ellipse in length and round across having an average size of about 5 mm in length and about 3 mm in diameter.
- *Petals*.—Five petals per floret, petals have an obvoate/elongated ellipse shape with an average length of about 6mm and average width of about 3 mm; colors: 47A on upper side of petal and 53C on underside of petal.
- *Hood*.—Five per floret, having a boat shape with an average length of about 3 mm and an average width of 1 mm; color: 21B.
- *Horn*.—Five per floret, having a needle shape with a length about 2 mm; color: S21B.
- *Sepals*.—Color 2D edged with 166A; having a spear-like shape with a length of about 2 mm and smooth surface texture.
- *Calyx*.—Color 2D edged with 166A.
- *Corona*.—Color 23A; having a 5-point star shape and an average size of about 15 mm in diameter.
- *Corolla*.—Color 53C top of corolla and 47A underside of corolla.
- *Peduncle*.—Color 145B; having a rod shape with an average length of about 25 mm and a smooth surface texture.
- *Pedicel*.—Color 145B having a rod shape with an average length of about 14 mm and a smooth surface texture.
- *Reproductive organs*.—Flowers include five stamens with two anthers each. The stamens are fixed to the base of the corolla and contact each other to make a stamen ring. Anthers are about 1.5 mm, winged and oblong and 2C in color. Stamens are about 2 mm. Pollinum (pollen mass) are attached by joined thread-like arms at the corpusculum. The corona has a hood and horn. Flowers include 2 pistils per floret with fused stigmas, a length of about 2 mm and 20B in color.

*Seed*.—Encased in 2-4 inch follicles. Follicles are variegated with a mixture of 136A, 146C, 8C, 4D, and 71A. Seeds are ovate, about 0.25 inch long, and vary in color from 166A to 165A. Average pappus length is about 6-8 mm. Average number of seeds per pod is undetermined but presumed to be similar to other Asclepias curassavica at about 60-80 seeds per follicle.

It is claimed:

1. A new and distinct cultivar of *Asclepias* plant named 'Charlotte's Blush' as herein illustrated and described.

* * * * *